(12) United States Patent
Béland

(10) Patent No.: US 6,193,730 B1
(45) Date of Patent: Feb. 27, 2001

(54) SURGICAL EXTRACTOR

(75) Inventor: Germain Béland, Sherbrooke (CA)

(73) Assignee: Instruments Médicaux G.B. Inc., Sherbrooke (CA)

( * ) Notice: Subject to any disclaimer, the term of this patent is extended or adjusted under 35 U.S.C. 154(b) by 0 days.

(21) Appl. No.: 09/440,060

(22) Filed: Nov. 15, 1999

(51) Int. Cl.$^7$ .............................. A61B 17/42; A61B 17/46
(52) U.S. Cl. ........................ 606/114; 606/110; 606/127; 606/128
(58) Field of Search ................................ 606/114, 113, 606/110, 185, 127, 128, 198, 191, 200, 206

(56) References Cited

U.S. PATENT DOCUMENTS

| | | |
|---|---|---|
| 4,347,846 | 9/1982 | Dormia . |
| 4,807,626 | 2/1989 | McGirr . |
| 5,064,428 * | 11/1991 | Cope et al. ........................ 606/127 |
| 5,147,371 | 9/1992 | Washington et al. . |
| 5,275,610 * | 1/1994 | Eberbach ............................ 606/198 |
| 5,339,803 * | 8/1994 | Mayzels et al. ..................... 606/198 |
| 5,656,012 | 8/1997 | Sienkiewicz . |
| 5,730,726 | 3/1998 | Klinggnstein . |
| 5,782,839 * | 7/1998 | Hart et al. ............................. 606/114 |
| 5,788,709 * | 8/1998 | Riek et al. ............................ 606/114 |

\* cited by examiner

Primary Examiner—Pedro Philogene
(74) Attorney, Agent, or Firm—Robic

(57) ABSTRACT

The surgical extractor has three distinct portions respectively called "body", "gripper" and "pusher". The body is rigid and rectilinear and has a first end from which an handle integrally projects perpendicularly to the longitudinal axis. The gripper consists of one or more flexible rods having first ends connected to the opposite end of the body in a foldable manner with respect to a transverse axis. The pusher is rigid and rectilinear and has a first end connected to the opposite ends of the straps and a second end provided with a pushing button. Hooks are provided for retaining in a slidable manner the pusher on top of the first end of the body opposite to the handle once the straps have been folded about the transverse axis in order to be positioned together with a pusher flat onto the body. These hooks allow the person pushing on the button while he/she holds the handle, to force the straps to open like petals on top of the body and thus makes it possible for the straps to catch in a radial direction an organ to be extracted from the body of the patient, and to grip this organ in order to remove it from the body of the patient.

20 Claims, 4 Drawing Sheets

SURGICAL EXTRACTOR

TECHNICAL FIELD OF THE INVENTION

The present invention relates to an apparatus hereinafter called "surgical extractor" which is intended to be used in surgery, and more specifically in laparoscopy, to extract an organ or an element of a non-negligible size from the body of a patient during an operation. Such organ can be, for example, the spleen, the appendix or an ovary.

BRIEF DESCRIPTION OF THE PRIOR ART

There are numerous patents disclosing surgical extractors, which are devised to remove stones or tissues from the body of a patient. By way of examples, reference can be made to the following U.S. patents:

U.S. Pat. No. 4,807,826 (1989) McGIRR
U.S. Pat. No. 4,547,371 (1992) WASHINGTON
U.S. Pat. No. 5,788,709 (1998) RIEK et al

There are also patents disclosing medical extractors. By way of non-restrictive example of such patents, reference can be made to the following U.S. patent which discloses an extractor devised for removing faecal imprecations from the rectum of a patient:

U.S. Pat. No. 5,730,726 (1998) KLINGENSTEIN

There are furthermore numerous patents disclosing in apparatuses known as "surgical retractors", which are used for separating or spacing away part of an organ or of the body of a patient during a surgery, especially a laparoscopy. By way of non-restrictive examples of such patents, reference can be made to the following U.S. patents:

U.S. Pat. No. 5,275,610 (1994) COOK INC.
U.S. Pat. No. 5,339,803 (1994) MAYZELS et al
U.S. Pat. No. 5,656,012 (1997) U.S. SURGICAL CORP.

If all these patents disclose apparatuses having a structure and a utility that may a priori be considered as similar to those of the extractor according to the invention, none of them discloses a surgical extractor which is of simple yet efficient structure and which is devised:

1—to open on one side only of its longitudinal axis, in order to grasp and catch with precision the organ to be extracted; and 2—to apply if need be a compression force onto the organ to be extracted after it has been grasped in order to reduce its side and thus to facilitate its extraction.

SUMMARY OF THE INVENTION

A first object to the present invention is to provide a surgical extractor intended to be used for extracting an organ from the body of a patient during an operation, which extractor is very simple in structure while being very efficient in use.

Another object of the invention is to provide a surgical extractor which satisfies the two above mentioned needs, thereby making it useful in laparoscopy for extracting through an orifice of small diameter (1 cm or less), organs of a non-negligible size which are in fact very superior to those of stones or tissues. By way of non-limitative examples of such of organs of non-negligible, reference can be made to the spleen, the appendix or the ovaries.

The surgical extractor according to the invention is characterized in that it comprises:

a first portion hereinafter called "body", which body is thin, rigid and rectilinear and has a longitudinal axis, a first end from which an handle integrally projects perpendicularly to the longitudinal axis, and a second end opposite to the first end;

a second portion hereinafter called "gripper", which consists of at least one flexible rod having a first end connected to the second end of the body in a foldable manner with respect to a transverse axis, said at least one rod also having a second opposite end a third portion hereinafter called "pusher", which is rigid and rectilinear and has a first end that is thin and connected to the second ends of the rods, and a second opposite end provided with a pushing button; and retaining means for retaining in a slidable manner the second end of the pusher onto the first end of the body, once the straps have been folded about the transverse axis in order to be positioned together with the pusher flat onto the body.

In use, when a person pushes on the button while he/she holds the handle, he/she forces the straps to bend and move away from the body and thus to make it possible for the straps to grasp in a radial direction an organ to be extracted from the body of a patient and to grip this organ in order to remove it from the body of the patient.

Preferably, the first end of the body has a portion adjacent to the handle that is U-shaped in transverse cross-section and is sized to receive the pusher in a sliding manner when the gripper and pusher are folded onto the body. In such a case, the retaining means consist of hooks which are located within the U-shaped portion at the first end of the body, and are positioned and sized to snap onto the pusher when the gripper and the pusher are folded onto the body.

Preferably also, the pusher is provided with radial slots positioned in such a manner as to lock in a removable manner onto the hooks located within the U-shaped portion of the first end of the body when the gripper and pusher are folded onto this body. In use, these slots allow the pusher to be locked into a given position relative to the body.

The invention and its advantages would be better understood upon reading the following non-descriptive description of a preferred embodiment of the invention, made with reference to the accompanying drawings.

Figure 1:
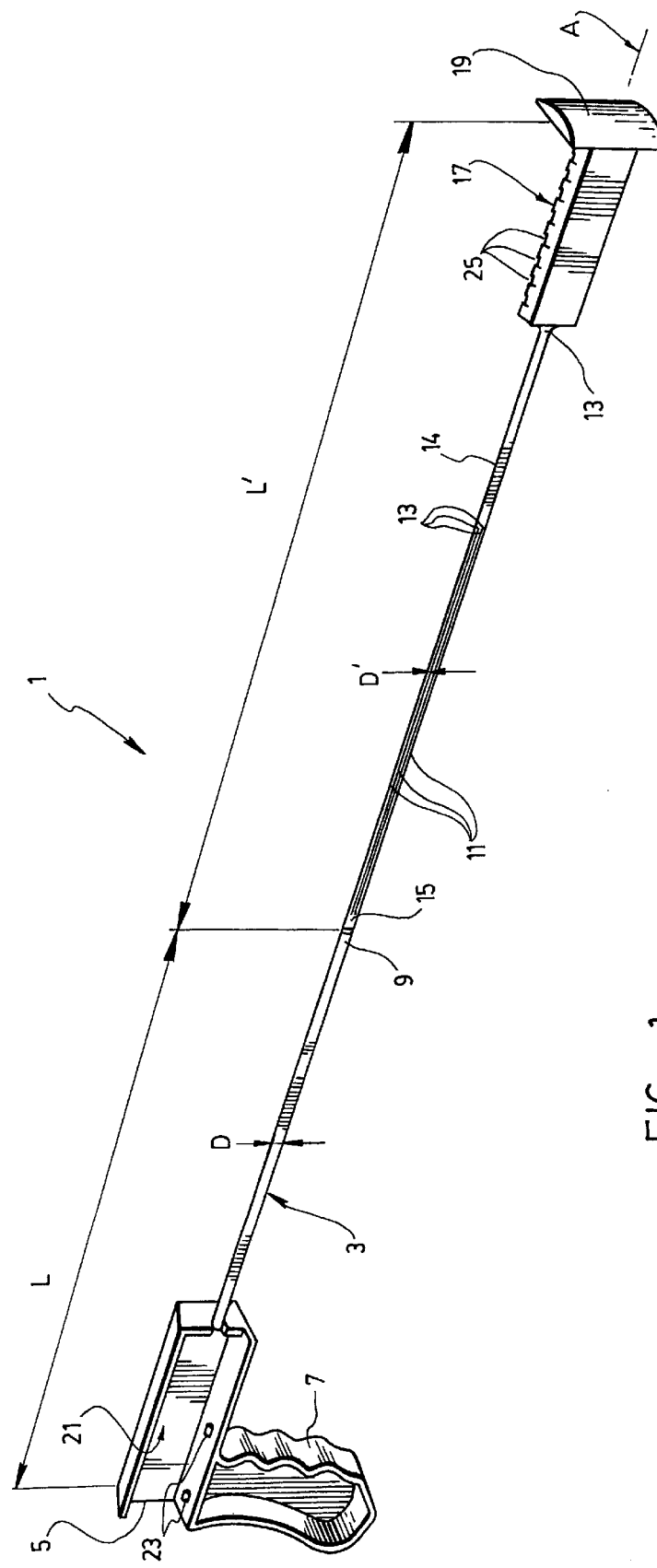
FIG. 1 is a perspective view of a surgical extractor according to a preferred embodiment of the invention, shown in unfolded position.

It is worth mentioning that the proportions used in the drawings are not illustrative of the real dimensions of the embodiment that will now be described. These proportions were used only for the purpose of making the invention easier to understand. To evaluate the real dimensions of the extractor according to the invention, reference should be made to the values given in the following description.

DESCRIPTION OF A PREFERRED EMBODIMENT OF THE INVENTION

The surgical extractor 1 according to the preferred embodiment of the invention shown in the accompanying drawings is made of plastic material of a biocompatible type. Preferably, the extractor 1 is made of a single molded piece. However, it could be made of distinct pieces that would be assembled after molding.

The extractor 1 comprises a first portion 3 hereinafter called "body", which is thin, rigid and rectilinear and has a longitudinal axis "A". The body 3 has a first end 5 from which a handle 7 integrally projects perpendicularly to the longitudinal axis. The body 3 also has a second end 9 which is opposite to the first one.

Figure 2:
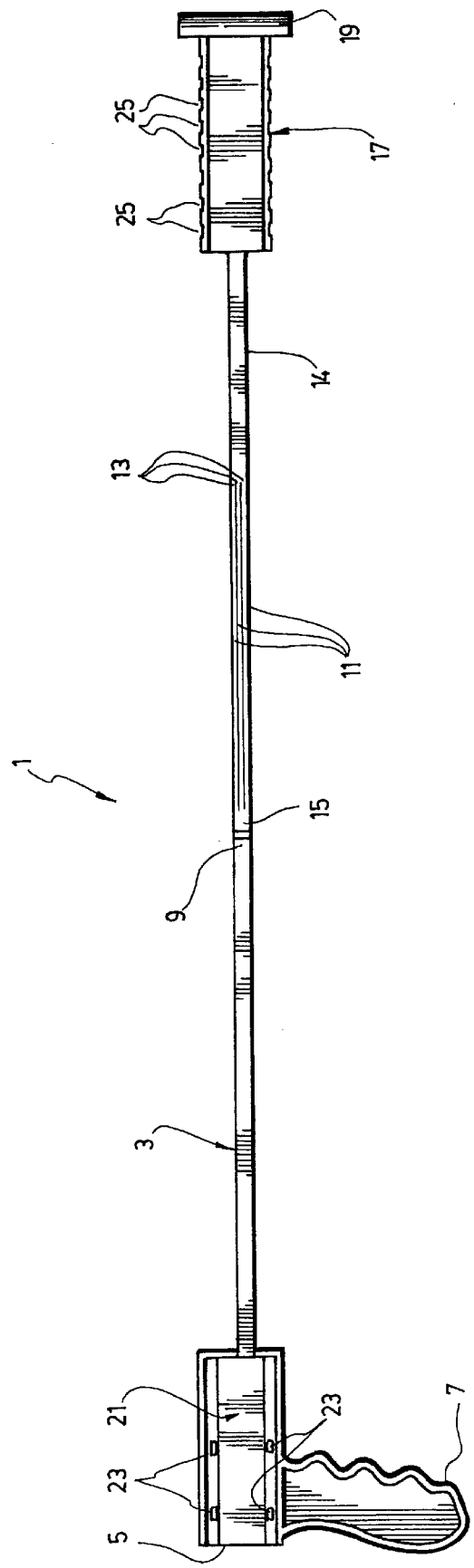
FIG. 2 is a side elevational view of the extractor as shown in FIG. 1.

The extractor 1 also comprises a second portion integral to the first one. This second portion hereinafter called "gripper", consists of three foldable rods 11 having first ends connected to the second end 9 of the body in a foldable manner with respect to a transversal axis "T". The rods also have second opposite ends 13. As is shown in the drawings, the rods 11 extend in a plane that is parallel to the handle when they are in line with the body (see FIGS. 1 and 2) or folded on it (see FIG. 3). It is worth noting that this particular arrangement is not actually essential to the invention. Indeed, the rods could extend in any other plane.

In the illustrated embodiment, the gripper consists of three rods 11 exclusively. However, use could be made of one or two rods only, or of more that three rods, the maximum number of rods being preferably equal to for obvious practical reasons.

Figure 3:
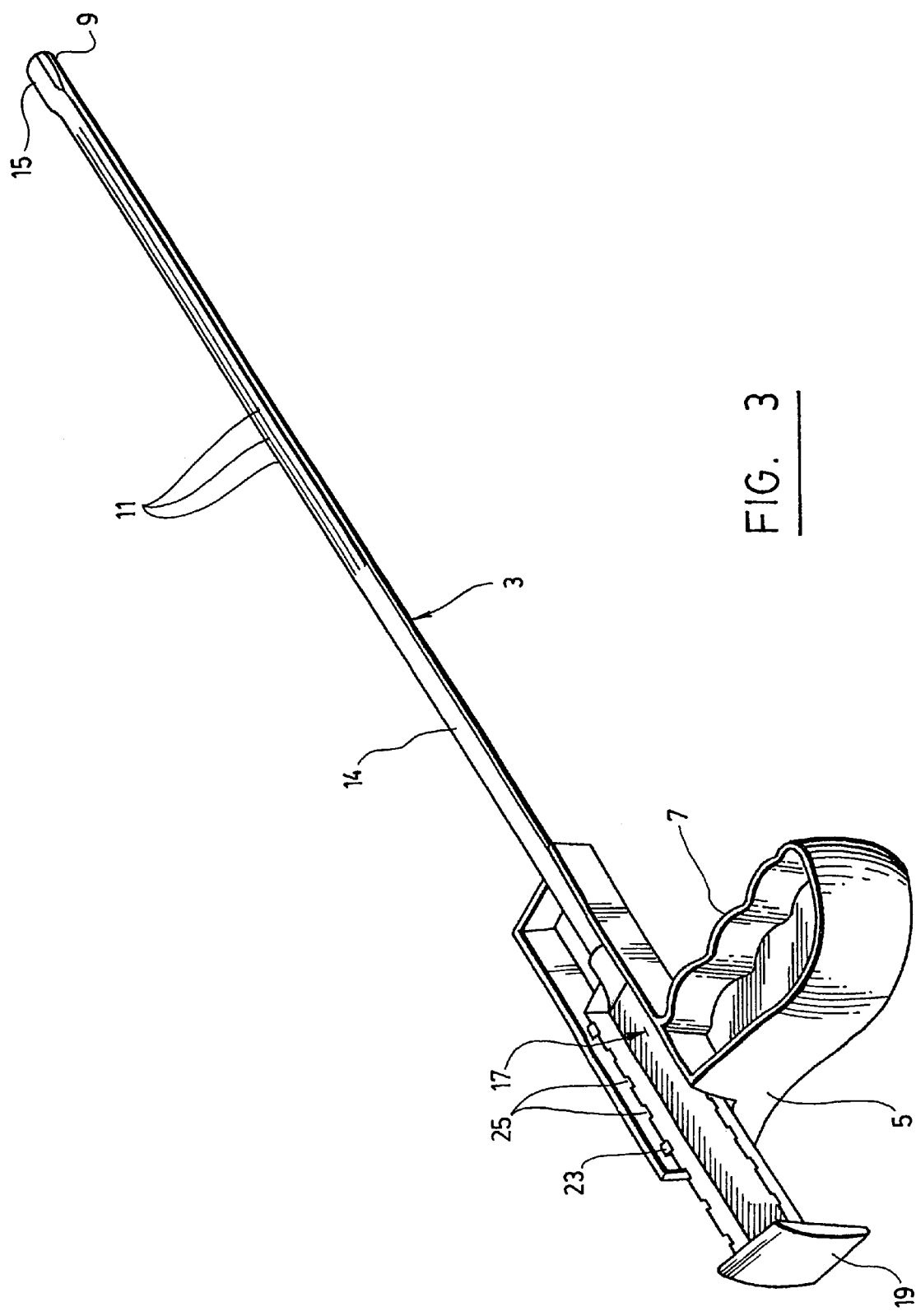
FIG. 3 is a perspective view of the extractor shown in FIGS. 1 and 2, when the gripper and pusher are folded onto the body and are in closed position.

Advantageously, to facilitate folding of the rods onto the body 3 in the position shown in FIG. 3, the rods 11 have their first ends connected to the second end 9 of the body through a weakened zone of reduced thickness allowing the requested folding with respect to the transverse axis T.

The surgical extractor 1 further comprises a third portion 17 hereinafter called "pusher", which, like the body 3, is rigid and rectilinear. The pusher 17 has a first end 14 that is thin and connected to the second ends 13 of the rods 11 and a second opposite end provided with an enlarged part acting as a pushing button 19.

In practice, the body preferably has a length "L" of about 40 cm and a diameter "D" of about 3 mm. The rods 11 and the pusher 17 altogether have a length "L'" of about 45 cm. The rods 11 have a diameter "D'" of about 1 mm and the pusher 17 has a diameter "D''" of about 3 mm. These dimensions may vary but those indicated hereinabove have the advantage of making the extractor 1 easy to mold, very efficient in use and, more importantly, useful as such in laparoscopy.

Retaining means are provided for retaining in a slidable manner the second end of the pusher 17 onto the first end 5 of the body 3 once the rods 11 are folded about the transverse axis "T" flat onto the body 3 in the position shown in FIG. 3 and the pusher 17 and gripper 11 then extend flat onto the body 3.

In the illustrated embodiment, the first end 5 of the body 3 has a portion 21 adjacent to the handle that is U-shaped in transverse cross-section and is sized to receive the second end (or rear portion) of the pusher 17 in a sliding manner when the gripper and pusher are folded onto the body. The retaining means consist of hooks 23 located within the U-shaped portion 21 at the first end 5 of the body. These hooks 23 are positioned on the side walls of the U-shaped portion and are sized to snap onto the pusher 17 when the gripper and the pusher are folded onto the body 3.

In practice, the first end of the body could have a different shape (it could be cylindrical and of the same diameter as the remaining of the body) and other retaining means could be used, such as external hooks or a ring. In fact, the only requirement is that these retaining means allow the pusher 17 to be slidably moved longitudinally with respect to the body 3 (see the arrow "X" in FIG. 3). Indeed, the purpose of these retaining means is to retain the pusher onto the body 3 while allowing a person pushing up to the button 19 while he/she holds the handle 7, to force the rods to bend and move away from the body. When such is done, it becomes possible for the straps to catch in a radial direction "R" an organ to be extracted from the body of the patient and to grip this organ in order to remove it from the body (see FIG. 4).

Advantageously, the pusher 17 can be provided with radial slots 25 positioned in such a manner as to lock in a removable manner onto the hooks 23 located within the U-shaped portion 21 of the first end 5 of the body 3 when the gripper and pusher are folded onto this body. These slots 25 allow the pusher to be locked into a given position relative to the body.

Figure 4:
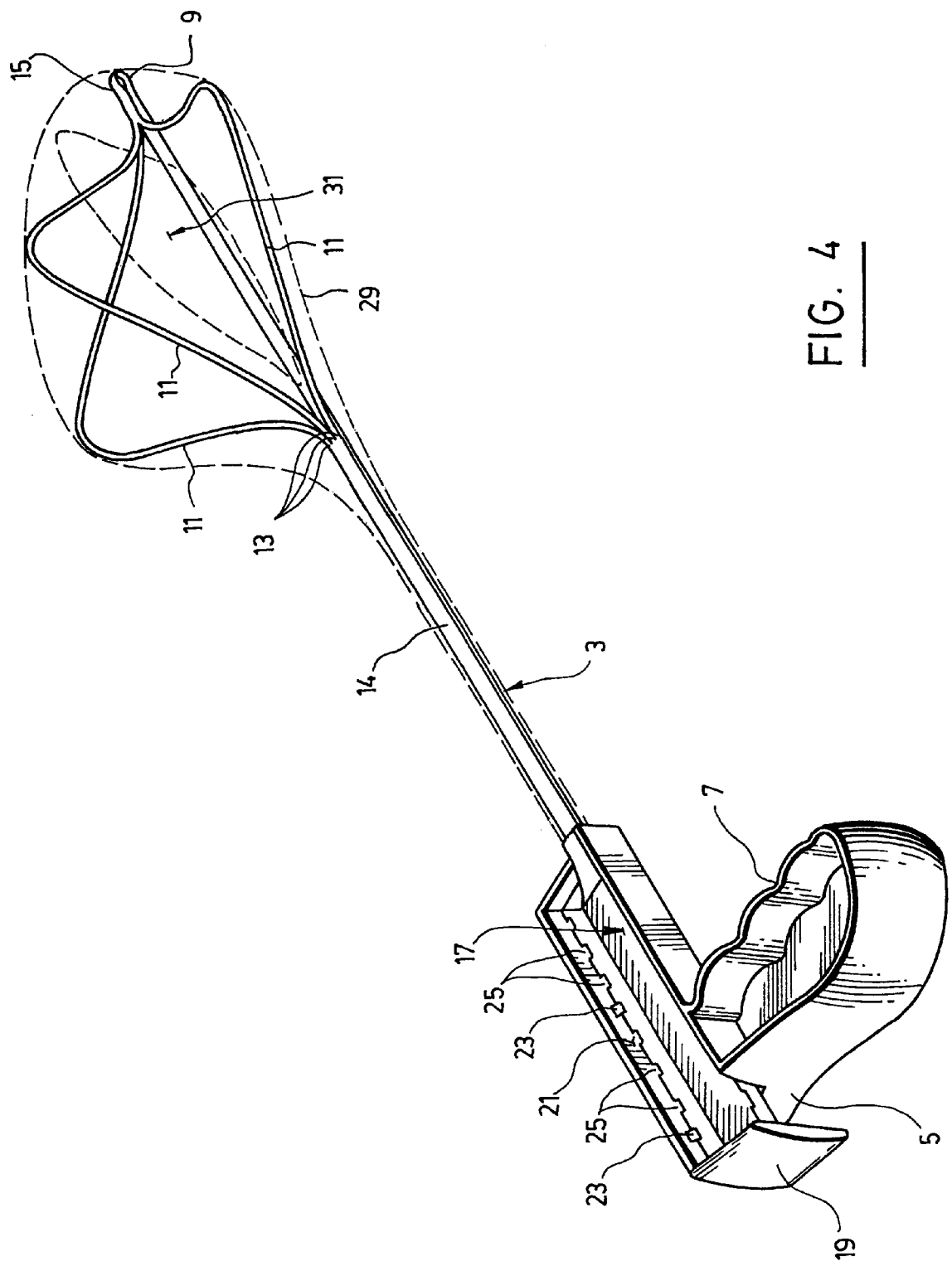
FIG. 4 is a perspective view similar to the one of FIG. 3, but showing the extractor in an open position ready to grasp an organ to be extracted.

As is shown in dotted line in FIG. 4, a sealing bag 29 having a rear portion provided with the radial slot 31 can be slipped onto the second end 9 of the extractor once the same is assembled so as to extend up to the portion 21 of the body that is adjacent to the handle 7. This bag has two purposes. First of all, its rear portion covers the second end 9 of the body and the rods 11 and thus acts as a "container" for receiving the organ to be extracted. For this purpose, the slot 31 of the bag 29 is positioned in such a manner as to extend between the rods 11 when the same are opened. When the pusher 17 is pushed in forward position (see FIG. 4), the rods 11 fold up and open the slot 31, thereby allowing the organ to be grasped and inserted into the bag 29. When the pusher moves in the rearward position (see FIG. 3), the bag 29 is close together with the rods 11 and prevents the organ and/or any crushed part thereof for escaping within the body of the patient.

Secondly, the front portion of the bag 29 which is shaped as a thin sleeve holds the first end 14 of the pusher 17 flat against the adjacent portion of the body and avoids that these elements move away from each other or be deformed if they are too much flexible. It is worth noting that, to ensure this holding, other means could be used, such a tongue-and-groove system that could be provided in the elements 14 and 3 to prevent the same from moving away from each other.

As may now be understood, the surgical extractor 1 according to the invention is particularly well adapted for use in laparoscopy. Thanks to its structure, it opens on one side only of its longitudinal axis, in the radial direction "R", in order to catch and grip with precision the organ to be extracted. The rods 11 may then be used to apply in a substantial compression force onto the organ to be extracted after it has been grasped in order to press it, crush it if need be and thus reduce its size to facilitate its extraction from the patient's body.

Of course, numerous modifications could be made to the preferred embodiment that has been disclosed hereinabove without departing from the scope of the present invention.

What is claimed is:

1. A surgical extractor comprising:
   a first portion hereinafter called <body>, said body being thin, rigid and rectilinear and having a longitudinal axis, a first end from which an handle integrally projects perpendicularly to the longitudinal axis, and a second end opposite to the first end;
   a second portion hereinafter called "gripper", said gripper consisting of at least one flexible rod having a first end connected in a foldable manner to the second end of the body with respect to a transverse axis, said at least one rod also having a second opposite end;

a third portion hereinafter called <pusher>, said pusher being rigid and rectilinear and having a first end that is thin and connected to the second end of said at least one rod and a second opposite end provided with a pushing button; and retaining means for retaining in a slidable manner the second end of the pusher onto the first end of the body, once said at least one rod of the gripper has been folded about the transverse axis in order to be positioned together with the pusher flat onto the body;

whereby, when a person pushes on the button while he/she holds the handle, he/she forces said at least one rod to bend and move away from the body and thus to make it possible for said at least one rod to catch in a radial direction an organ to be extracted from the body of a patient and to grip said organ in order to remove it from the body of the patient.

2. The surgical extractor of claim 1, wherein the gripper consists of two to six of said at least one flexible rod.

3. The surgical extractor of claim 2, wherein the gripper consists of three of said at least one flexible rod.

4. The surgical extractor of claim 2, wherein the flexible rods have their first ends connected to the second end of the body through a weakened zone of reduced thickness allowing the requested folding with respect to the transverse axis.

5. The surgical extractor of claim 1, wherein:

the first end of the body has a portion adjacent to the handle that is U-shaped in transverse cross-section and is sized to receive the pusher in a sliding manner when the gripper and pusher are folded onto the body; and said retaining means consist of hooks located within the U-shaped portion at the first end of the body, said hooks being positioned and sized to snap onto the pusher when the gripper and the pusher are folded onto the body.

6. The surgical extractor of claim 4, wherein:

the first end of the body has a portion adjacent to the handle that is U-shaped in transverse cross-section and is sized to receive the pusher in a sliding manner when the gripper and pusher are folded onto the body; and said retaining means consist of hooks located within the U-shaped portion at the first end of the body, said hooks being positioned and sized to snap onto the pusher when the gripper and the pusher are folded onto the body.

7. The surgical extractor of claim 6, wherein the pusher is provided with radial slots positioned in such a manner as to lock in a removable manner onto the hooks located within the U-shaped portion of the first end of the body when the gripper and pusher are folded onto said body, said slots allowing the pusher to be locked into a given position relative to the body.

8. The surgical extractor of claim 2, which is made of plastic material and wherein:

the body has a length of about 40 cm and a diameter of about 3 mm;

the gripper and pusher altogether have a length of about 45 cm;

said at least one rod has a diameter of 1 mm; and the pusher has a diameter of 3 mm.

9. The surgical extractor of claim 5, which is made of plastic material and wherein:

the body has a length of about 40 cm and a diameter of about 3 mm;

the gripper and pusher altogether have a length of about 45 cm;

said at least one rod has a diameter of 1 mm; and the pusher has a diameter of 3 mm.

10. The surgical extractor of claim 7, which is made of plastic material and wherein:

the body has a length of about 40 cm and a diameter of about 3 mm;

the gripper and pusher altogether have a length of about 45 cm;

said at least one rod has a diameter of 1 mm; and the pusher has a diameter of 3 mm.

11. The surgical extractor of claim 2, which is made of a single molded piece.

12. The surgical extractor of claim 8, which is made of a single molded piece.

13. The surgical extractor of claim 9, which is made of a single molded piece.

14. The surgical extractor of claim 10, which is made of a single molded piece.

15. The surgical extractor of claim 2, further comprising:

a sealing bag having a front portion and a rear portion provided with a radial slot, said bag being slipped onto the extractor once the same is assembled, the front portion of said bag being shaped as a sleeve and acting as attachment means to hold the first end of the pusher against the body, the rear portion of said bag acting as a container for receiving the organ to be extracted.

16. The surgical extractor of claim 5, further comprising:

a sealing bag having a front portion and a rear portion provided with a radial slot, said bag being slipped onto the extractor once the same is assembled, the front portion of said bag being shaped as a sleeve and acting as attachment means to hold the first end of the pusher against the body, the rear portion of said bag acting as a container for receiving the organ to be extracted.

17. The surgical extractor of claim 7, further comprising:

a sealing bag having a front portion and a rear portion provided with a radial slot, said bag being slipped onto the extractor once the same is assembled, the front portion of said bag being shaped as a sleeve and acting as attachment means to hold the first end of the pusher against the body, the rear portion of said bag acting as a container for receiving the organ to be extracted.

18. The surgical extractor of claim 9, further comprising:

a sealing bag having a front portion and a rear portion provided with a radial slot, said bag being slipped onto the extractor once the same is assembled, the front portion of said bag being shaped as a sleeve and acting as attachment means to hold the first end of the pusher against the body, the rear portion of said bag acting as a container for receiving the organ to be extracted.

19. The surgical extractor of claim 10, further comprising:

a sealing bag having a front portion and a rear portion provided with a radial slot, said bag being slipped onto the extractor once the same is assembled, the front portion of said bag being shaped as a sleeve and acting as attachment means to hold the first end of the pusher against the body, the rear portion of said bag acting as a container for receiving the organ to be extracted.

20. The surgical extractor of claim 12, further comprising:

a sealing bag having a front portion and a rear portion provided with a radial slot, said bag being slipped onto the extractor once the same is assembled, the front portion of said bag being shaped as a sleeve and acting as attachment means to hold the first end of the pusher against the body, the rear portion of said bag acting as a container for receiving the organ to be extracted.

* * * * *